(12) United States Patent
Fu

(10) Patent No.: US 6,315,881 B1
(45) Date of Patent: *Nov. 13, 2001

(54) ELECTRIC CELLS AND GAS SENSORS USING ALKALI ION CONDUCTIVE GLASS CERAMIC

(75) Inventor: Jie Fu, Sagamihara (JP)

(73) Assignee: Kabushiki Kaisha Ohara, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/289,242

(22) Filed: Apr. 9, 1999

Related U.S. Application Data

(63) Continuation-in-part of application No. 08/923,233, filed on Sep. 4, 1997, now abandoned.

(30) Foreign Application Priority Data

| Nov. 15, 1995 | (JP) | ................................................... | 7-320971 |
| Apr. 12, 1996 | (JP) | ................................................... | 8-115694 |
| Feb. 6, 1997 | (JP) | ................................................... | 9-38303 |

(51) Int. Cl.$^7$ ...................... G01N 27/406; C03C 10/10; C03C 4/18

(52) U.S. Cl. .............................. 204/424; 204/426; 501/4; 501/46; 501/48; 501/73

(58) Field of Search ............................... 501/3, 4, 10, 46, 501/48, 73; 429/193, 33; 252/518; 204/424, 425, 426, 427, 428, 429

(56) References Cited

U.S. PATENT DOCUMENTS

| 4,985,317 | * | 1/1991 | Adachi ................................. | 429/191 |
| 5,492,610 | * | 2/1996 | Behl et al. ............................ | 204/421 |

FOREIGN PATENT DOCUMENTS

| 0718247 | 6/1996 | (EP) . |
| 2225310 | 9/1990 | (JP) . |
| 02302307 | 12/1990 | (JP) . |
| 329206 | 2/1991 | (JP) . |
| 794013 | 4/1995 | (JP) . |

OTHER PUBLICATIONS

Sadaoka "Ionic conductivity of alkali–rare earth silicate and its application as a solid–state electrochemical CO2 gas sensor", Defect and Diffusion Forum vol. 117–118, pp. 129–144, 1995.*

Min et al "The effects of mixed glass formers on the properties on non–crystalline lithium ion conductors", Phys. Stat. Sol. (a), 148, pp. 383–388, 1995.*

(List continued on next page.)

*Primary Examiner*—Robert J. Warden, Sr.
*Assistant Examiner*—Kaj K. Olsen
(74) *Attorney, Agent, or Firm*—Hedman & Costigan, P.C.

(57) ABSTRACT

A solid electric cell includes a case, a negative electrode, a positive electrode and a solid electrolyte. The negative electrode, positive electrode and solid electrolyte are disposed in the case in such a manner that the negative electrode opposes the positive electrode through the solid electrolyte. The solid electrolyte is made of an alkali ion conductive glass-ceramic having ion conductivity no less than $10^{-3}$S/cm at room temperature. A gas sensor includes a case, a negative electrode, a positive electrode, a solid electrolyte and a layer for which an electromotive force corresponding to the concentration of the gas is produced between the two electrodes. In the case, the negative electrode opposes the positive electrode through the solid electrolyte. The solid electrolyte is made of an alkali ion conductive glass-ceramic having ion conductivity no less than $10^{-3}$S/cm at room temperature.

23 Claims, 3 Drawing Sheets

OTHER PUBLICATIONS

Umegaki et al "Development of Na+–superionic conductors using new rare–earth silicophosphate materials by means of glass–ceramic processing", New Funct. Mater., vol. C, (CAS bib and abstract only), 1993.*

Cretin, M. et al., J. Eur. Ceramic Soc., vol. 15, No. 11 (1995) 1149–1156.

Patent Abstracts of Japan, vol. 017, No. 513, Sep. 16, 1993.

Patent Abstracts of Japan, vol. 097, No. 010, Oct. 31, 1997.

Jie, F., Solid State Ionics, vol. 96, No. 3, Apr. 1997, 195–200.

* cited by examiner

ELECTRIC CELLS AND GAS SENSORS USING ALKALI ION CONDUCTIVE GLASS CERAMIC

This invention relates to a continuation-in-par of Ser. No. 08/923,233 filed on Sep. 4, 1997 now abandoned.

BACKGROUND OF THE INVENTION

This invention relates to wholly solid electric cells and gas sensors and, more particularly, to electric cells and gas sensors using an alkali ion conductive glass-ceramics.

Recent development in electronics has brought about high-performance electronic devices of a compact and light-weight design and, as a power source of such electronic devices, development of an electric cell of a high energy density and a long life is strongly desired for.

Lithium has the highest oxidation-reduction potential of $Li/Li^+$ of all metal elements and has the smallest mass per 1 mol and, therefore, lithium cell can provide a higher energy density than other types of cells. Moreover, if a lithium ion conductive solid electrolyte is used, a cell of a thin film can be formed and increase in energy density per unit volume can thereby be realized.

A lithium ion cell which has been realized to date uses an organic electrolyte solution as its electrolyte and this makes it difficult to achieve a cell of a compact design such as a thin film design. This lithium ion cell has additional disadvantages that it has likelihood of spontaneous combustion. If this lithium ion cell is replaced by a cell employing an inorganic solid electrolyte, a wholly solid cell of a high reliability will be realized. For this reason, studies and development of a solid electrolyte having a high conductivity have been vigorously made for realizing a wholly solid lithium cell.

Moreover, carbon dioxide gas produced by combustion of fossil fuel is a main cause of a hothouse effect which has recently become a serious problem and it has become necessary to incessantly watch the concentration of carbon dioxide gas. Therefore, establishment of a system for detecting carbon dioxide gas is a matter of increasing importance for the maintenance of a comfortable life in the future human society.

Carbon dioxide gas detection system which are currently in use are generally of a type utilizing absorption of infrared ray. These systems however are large and costly and besides are very susceptible to contamination. For these reasons, studies have recently been actively made to develop a compact carbon dioxide gas sensor using a solid electrolyte. Particularly, many reports have been made about studies using a lithium ion solid electrolyte.

For realizing such gas sensor using solid electrolyte, development of a solid electrolyte which is highly conductive, chemically stable and sufficiently heat proof is indispensable.

Among known electrolytes, $Li_3N$ single crystal (Applied Physics letter, 30(1977) 621–22) and $LiI$—$Li_2S$—$P_2S_5$, $LiI$—$Li_2S$—$SiS_4$ and $LiI$—$Li_2S$—$B_2S_3$ glasses (Mat. Res. Bull., 18(1983) 189) have high conductivity of $10^{-3}$ S/cm or over. These materials, however, have the disadvantages that preparation and handling of these materials are difficult and these materials are not sufficiently heat proof. Particularly, these materials have the fatal disadvantage that decomposition voltage of these materials is so low that, when they are used for an electrolyte of a solid cell, a sufficiently high terminal voltage cannot be obtained.

An oxide lithium solid electrolyte does not have the above described disadvantages and has a decomposition voltage which is higher than 3V and, therefore, it has possibility of usage as a wholly solid lithium cell if it exhibits a high conductivity at room temperature. It is known in the art that conductivity in an oxide glass can be increased by increasing lithium ion concentration. However, there is limitation in increasing the lithium ion concentration even if rapid quenching is employed for glass formation and conductivity of this glass at room temperature is below $10^{-6}$ S/cm at the highest.

Japanese Patent Application Laid-open Publication No. Hei-8-2239218 discloses a gas sensor using a thin film of lithium ion conductive glass. The conductivity of this lithium ion conductive glass thin film is between $1.7 \times 10^{-7}$ and $6.1 \times 10^{-7}$. This is not a sufficiently high value and a solid electrolyte having a higher conductivity is desired for.

An oxide ceramic having the highest conductivity at room temperature is $Li_{1+X}Al_XTi_{2-X}(PO_4)_3$. When X is 0.3, the conductivity thereof is $7 \times 10^{-4}$ S/cm at room temperature (J. Electrochem. Soc. 137(1990) 1023). Oxide ceramics are superior in conductivity to glasses but have the disadvantages that they require a troublesome process for manufacturing and that they are difficult to form, particularly to a thin film.

In short, the prior art lithium ion solid electrolyte have the problem that they are either low in conductivity, hard to handle, hard to form to a compact design such as a thin film.

It is, therefore, an object of the invention to provide an electric cell and a gas sensor of a high performance which have solved these problems.

SUMMARY OF THE INVENTION

As described above, $Li_{1+X}Al_XTi_{2-X}(PO_4)_3$ ceramics exhibit conductivity of $10^{-4}$ S/cm or over at room temperature. These ceramics, however, have pores and a large grain boundary which can not be eliminated completely and existence of these pores and grain boundary results in a decrease in conductivity. If, therefore, glass-ceramics including the above crystal are provided, there will be no pores and the grain boundary will be improved and, as a result, a solid electrolyte having a higher conductivity is expected to be provided. Besides, glass-ceramics which share a feature of glass can be easily formed into various shapes including a thin film by utilizing this feature of glass. For these reasons, glass-ceramics are considered to have practical advantages over ceramics made by sintering.

As a result of studies and experiments made by the inventor of the present invention on the basis of the above described basic concept, the inventor has succeeded in obtaining glass-ceramics having a very high lithium ion conductivity no less than $10^{-3}$ S/cm at room temperature by producing glasses including the ingredients of the above described crystal and causing the crystal phase to grow from these glasses by heat treating these glasses, and further succeeded in developing a novel electric cell and gas sensor of a very high performance by utilizing these glass-ceramics.

The inventor of the present invention has also succeeded in obtaining glass-ceramics having the high lithium ion conductivity no less than $10^{-3}$ S/cm at room temperature by producing glasses including ingredients of $P_2O_5$, $SiO_2$, $TiO_2$, $M_2O_3$ (where M is Al or Ga) and $Li_2O$ and causing a crystal phase of a conductive crystal $Li_{1+X+Y}M_XTi_{2-X}Si_YP_{3-Y}O_{12}$ to grow from the glasses by heat treating these glasses, and further succeeded in utilizing these glass-ceramics for developing a novel electric cell and gas sensor.

According to the invention, there are provided electric cells and gas sensors wherein the solid electrolyte is made of an alkali ion conductive glass-ceramics which exhibit a very high conductivity no less than $10^{-3}$S/cm at room temperature. In addition to having the high conductivity, the glass-ceramics used in the electric cells and gas sensors made according to the invention have such an excellent formability that they can be easily formed into various shapes including a thin film, and they are thermally and chemically stable so that they are suitable for use as electrolytes of wholly solid cells and gas sensors. Therefore, the electric cells and gas sensors made according to the invention have a very high performance which can never be attained by the prior art electric cells and gas sensors.

For achieving the above described object of the invention, there is provided a solid electric cell comprising a case, a negative electrode, a positive electrode and a solid electrolyte, the negative electrode, positive electrode and solid electrolyte being disposed in the case in such a manner that the negative electrode opposes the positive electrode through the solid electrolyte characterized in that the solid electrolyte is made of an alkali ion conductive glass-ceramic having ion conductivity no less than $10^{-3}$S/cm at room temperature.

In one aspect of the invention, said alkali ion conductive glass-ceramic is a lithium ion conductive glass-ceramic.

In another aspect of the invention, there is provided a solid electric cell comprising a case, a negative electrode, a positive electrode and a solid electrolyte, the negative electrode, positive electrode and solid electrolyte being disposed in the case in such a manner that the negative electrode opposes the positive electrode through the solid electrolyte characterized in that the solid electrolyte is made of a lithium ion conductive glass-ceramic comprising 38–40 mol % of $P_2O_5$ and containing $Li_{1+X}(Al,Ga)_X Ti_{2-X}(PO_3)_4$ (where 0<X<0.8) as a main crystal phase.

In another aspect of the invention, said lithium ion conductive glass-ceramic comprises in mol %:

| | |
|---|---|
| $P_2O_5$ | 38–40% |
| $TiO_2$ | 25–45% |
| $M_2O_3$ (where M is Al or Ga) | 5–15% |
| $Li_2O$ | 10–20%. |

In another aspect of the invention, said lithium ion conductive glass-ceramic comprises in mol %:

| | |
|---|---|
| $P_2O_5$ | 38–40% |
| $TiO_2$ | 30–45% |
| $Al_2O_3$ | 5–15% |
| $Li_2O$ | 10–16%. |

In another aspect of the invention, said lithium ion conductive glass-ceramic comprises in mol %:

| | |
|---|---|
| $P_2O_5$ | 38–40% |
| $TiO_2$ | 25–45% |
| $Ga_2O_3$ | 5–12% |
| $Li_2O$ | 10–20%. |

In another aspect of the invention, there is provided a solid electric cell comprising a case, a negative electrode, a positive electrode and a solid electrolyte, the negative electrode, positive electrode and solid electrolyte being disposed in the case in such a manner that the negative electrode opposes the positive electrode through the solid electrolyte characterized in that the solid electrolyte is made of a lithium ion conductive glass-ceramic containing $Li_{1+X+Y}M_X Ti_{2-X}Si_Y P_{3-Y}O_{12}$ (where $0<X\leq 0.4$ and $0<Y\leq 0.6$) as a main crystal phase.

In another aspect of the invention, said lithium ion conductive glass-ceramic comprises in mol %:

| | |
|---|---|
| $P_2O_5$ | 26–40% |
| $SiO_2$ | 0.5–12% |
| $TiO_2$ | 30–45% |
| $M_2O_3$ (where M is Al or Ga) | 5–10% |
| $Li_2O$ | 10–18%. |

In another aspect of the invention, said lithium ion conductive glass-ceramic comprises in mol %:

| | |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18%. |

In another aspect of the invention, said lithium ion conductive glass-ceramic comprises in mol %

| | |
|---|---|
| $P_2O_5$ | 26–40% |
| $SiO_2$ | 0.5–12% |
| $TiO_2$ | 32–45% |
| $Ga_2O_3$ | 5–10% |
| $Li_2O$ | 10–18%. |

In another aspect of the invention, said alkali ion conductive glass-ceramic is substantially poreless.

In another aspect of the invention, there is provided a solid electric cell comprising a case, a negative electrode, a positive electrode and a solid electrolyte, the negative electrode, positive electrode and solid electrolyte being disposed in the case in such a manner that the negative electrode opposes the positive electrode through the solid electrolyte characterized in that the solid electrolyte is made of an alkali ion conductive glass-ceramic having a crsytal phase to grow from glasses by heat treating these glasses wherein said glasses have a composition range outside of the stoichiometry of the crystal.

In another aspect of the invention, said glasses are produced by employing a conventional glass melting method.

It has unexpectedly been found that the glasses from which the crystal of $Li_{1+X}(Al, Ga)_X Ti_{2-X}(PO_4)_3$ or $Li_{1+X+Y}M_X Ti_{2-X}Si_Y P_{3-Y}O_{12}$ grows have a composition range outside of the stoichiometry of the crystal and, for an unknown reason, the glass-ceramics having these specific crystal phases exhibit the high ion conductivity no less than $10^{-3}$S/cm at room temperature.

In prior art alkali ion conductive glass-ceramics such as those disclosed in U.S. Pat. No. 4,784,976, the stoichiometry of the crystals of these glass-ceramics exists in a composition ranges of glasses from which the crystals grow, and these prior art glass-ceramics have a significantly lower ion conductivity than the glass-ceramics used in the present invention.

In another aspect of the invention, there is provided a gas sensor comprising a case, a negative electrode, a positive electrode, a solid electrolyte and a layer for which an electromotive force corresponding to the concentration of the gas is produced between the two electrodes, a lead connected to the negative electrode and a lead connected to the positive electrode, the negative electrode, positive electrode and solid electrolyte being disposed in the case in such a manner that the negative electrode opposes the positive electrode through the solid electrolyte characterized in that the solid electrolyte is made of an alkali ion conductive glass-ceramic having ion conductivity no less than $10^{-3}$S/cm at room temperature.

In another aspect of the invention, said alkali ion conductive glass-ceramic is a lithium ion conductive glass-ceramic.

In another aspect of the invention, there is provided a gas sensor comprising a case, a negative electrode, a positive electrode, a solid electrolyte and a layer for which an electromotive force corresponding to the concentration of the gas is produced between the two electrodes, a lead connected to the negative electrode and a lead connected to the positive electrode, the negative electrode, positive electrode and solid electrolyte being disposed in the case in such a manner that the negative electrode opposes the positive electrode through the solid electrolyte characterized in that the solid electrolyte is made of a lithium ion conductive glass-ceramic comprising 38–40 mol % $P_2O_5$ and containing $Li_{1+x}(Al, Ga)_xTi_{2-x}(PO_4)_3$ (where 0<X<0.8) as a main crystal phase.

In another aspect of the invention, said lithium ion conductive glass-ceramic comprises in mol %:

| | |
|---|---|
| $P_2O_5$ | 38–40% |
| $TiO_2$ | 25–45% |
| $M_2O_3$ where M is Al or Ga | 5–15% |
| $Li_2O$ | 10–20%. |

In another aspect of the invention, said lithium ion conductive glass-ceramic comprises in mol %:

| | |
|---|---|
| $P_2O_5$ | 38–40% |
| $TiO_2$ | 30–45% |
| $Al_2O_3$ | 5–15% |
| $Li_2O$ | 10–16%. |

In another aspect of the invention, said lithium ion conductive glass-ceramic comprises in mol %:

| | |
|---|---|
| $P_2O_5$ | 38–40% |
| $TiO_2$ | 25–45% |
| $Ga_2O_3$ | 5–12% |
| $Li_2O$ | 10–20%. |

In another aspect of the invention, there is provided a gas sensor comprising a case, a negative electrode, a positive electrode, a solid electrolyte and a layer for which an electromotive force corresponding to the concentration of the gas is produced between the two electrodes, a lead connected to the negative electrode, and a lead connected to the positive electrode, the negative electrode, positive electrode and solid electrolyte being disposed in the case in such a manner that the negative electrode opposes the positive electrode through the solid electrolyte characterized in that the solid electrolyte is made of a lithium ion conductive glass-ceramic containing $Li_{1+X+Y}M_XTi_{2-X}Si_YP_{3-Y}O_{12}$ (where 0<X≦0.4 and 0<Y≦0.6) as a main crystal phase.

In another aspect of the invention, said lithium ion conductive glass-ceramic comprises in mol %:

| | |
|---|---|
| $P_2O_5$ | 26–40% |
| $SiO_2$ | 0.5–12% |
| $TiO_2$ | 30–45% |
| $M_2O_3$ (where M is Al or Ga) | 5–10% |
| $Li_2O$ | 10–18%. |

In another aspect of the invention, said lithium ion conductive glass-ceramic comprises in mol %:

| | |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18%. |

In another aspect of the invention, said lithium ion conductive glass-ceramic comprises in mol %:

| | |
|---|---|
| $P_2O_5$ | 26–40% |
| $SiO_2$ | 0.5–12% |
| $TiO_2$ | 32–45% |
| $Ga_2O_3$ | 5–10% |
| $Li_2O$ | 10–18%. |

In another aspect of the invention, the gas sensor is a carbon dioxide gas sensor and said layer is a metal carbonate layer.

In another aspect of the invention, there is provided a gas sensor comprising a case, a negative electrode, a positive electrode, a solid electrolyte and a layer for which an electromotive force corresponding to the concentration of the gas is produced between the two electrodes, a lead connected to the negative electrode and a lead connected to the positive electrode, the negative electrode, positive electrode and solid electrolyte being disposed in the case in such a manner that the negative electrode opposes the positive electrode through the solid electrolyte characterized in that the solid electrolyte is made of an alkali ion conductive glass-ceramic having a crystal phase to grow from glasses by heat treating these glasses wherein said glasses have a composition range outside of the stoichiometry of the crystal.

In another aspect of the invention, said alkali ion conductive glass-ceramic is substantially poreless.

In still another aspect of the invention, said glasses are produced by employing a conventional glass melting method.

DETAILED DESCRIPTION OF THE INVENTION

The composition of the glass-ceramics used as the solid electrolyte of the electric cell and gas sensor of the invention are expressed on the basis of composition of oxides in their base glasses. The above described content ranges of the respective ingredients have been selected for the reasons stated below.

In the ternary system $P_2O_5$—$TiO_2$—$Li_2O$, glass forming region exists in a very narrow range and the composition identical with that of $Li_{1+x}Al_xTi_{2-x}(PO_4)_3$ does not form glass when X is 0 (Bulletin of the Chemical Society of Japan, 51(1978) 2559). In the $P_2O_5$—$TiO_2$—($Al_2O_3$, $Ga_2O_3$)—$Li_2O$ system including $Al_2O_3$ or $Ga_2O_3$, a glass forming range has not been reported yet. Neither has been reported any glass-ceramic which has been prepared from such systems for obtaining a high lithium ion conductivity.

The inventor of the present invention has examined the glass forming range of the $P_2O_3$—$TiO_2$—($A_2O_3$, $Ga_2O_3$)—$Li_2O$ system by employing a conventional glass melting method and obtained lithium ion solid electrolytes of a high conductivity which can be classified within the following composition ranges (expressed in mol %) and can grow, as a result of heat treatment, $Li_{1+x}(Al, Ga)_xT_{2-x}(PO_4)_3$ as a main crystal phase.

In the case of the system including $Al_2O_3$,

| | |
|---|---|
| $P_2O_5$ | 38–40% |
| $TiO_2$ | 30–45% |
| $Al_2O_3$ | 5–15% |
| $Li_2O$ | 10–16% |

In the case of a system including $Ga_2O_3$,

| | |
|---|---|
| $P_2O_5$ | 38–40% |
| $TiO_2$ | 25–45% |
| $Ga_2O_3$ | 5–12% |
| $Li_2O$ | 10–20% |

In the case of a system including both $Al_2O_3$ and $Ga_2O_3$,

| | |
|---|---|
| $P_2O_5$ | 38–40% |
| $TiO_2$ | 25–45% |
| $Al_2O_3$, $Ga_2O_3$ | 5–15% |
| $Li_2O$ | 10–20% |

It has been found that a glass forming region exists beyond the above described composition ranges but, after a heat treatment, an electrolyte having a high conductivity could not be obtained from such composition range outside of the above described composition ranges. The above described composition ranges of the glass-ceramics of the invention have been determined on the basis of these experiments.

The glasses from which the crystal of $Li_{1+x}(Al, Ga)_xTi_{2-x}(PO_4)_3$ grows have a composition range which is outside of the stoichiometry of the crystal because the content range of $P_2O_5$ is 38–40 mol % whereas the stoichiometric content of $P_2O_5$ is 37.5 mol % in the crystal of $Li_{1+x}(Al, Ga)_xTi_{2-x}(PO_4)_3$.

In this system, a part of Al or Ga ingredients may be replaced by one of such trivalent metal elements as B, In, Sc, Fe and Cr. In this case, however, the amount of Al or Ga replaced by such metal element should not exceed 5%. If the amount of the replaced metal element exceeds 5%, conductivity will drop significantly.

A method for manufacturing the conductive glass-ceramics of the $P_2O_5$—$TiO_2$—($Al_2O_3$, $Ga_2O_3$)—$Li_2O$ system will now be described.

Starting materials are weighed at a predetermined ratio and mixed uniformly and the mixed materials are thereafter put in a platinum crucible and heated and melted in an electric furnace. First, gas components coming from the raw materials are evaporated at 700° C. and then the temperature is raised to 1400° C. to 1450° C. and the materials are melted at this temperature for about one to two hours. Then the melt is cast onto a stainless steel plate to form a sheet glass. The resultant glass is subjected to heat treatment within the temperature range from 800° C. to 1000° C. for 10 to 72 hours and lithium ion conductive glass-ceramics containing $Li_{1+x}(Al, Ga)_xTi_{2-x}(PO_4)_3$ as a main crystal phase were thereby produced.

A heat treatment at a higher temperature within the above described temperature range will be desirable if micro cracks are not produced because a heat treatment at a higher temperature will reduce the heat treating time. Generally speaking, a heat treatment performed at a temperature which is higher by about 300° C. than a crystallization temperature of the glass will be most effective because it will provide the highest conductivity.

In the case of the glass-ceramics made of $P_2O_5$—$SiO_2$—$TiO_2$—($Al_2O_3$, $Ga_2O_3$)—$Li_2O$ system which is used for the electric cells and gas sensors of the invention, the above described composition ranges have been selected because, within these composition ranges, dense glass-ceramics containing $Li_{1+X+Y}M_XTi_{2-X}Si_YP_{3-Y}O_{12}$ (where $0<X\leq0.4$, $0<Y\leq0.6$) as a main crystal phase and exhibiting a high lithium ion conductivity at room temperature were obtained by heat treating glasses of the same composition ranges. It has been found that the same crystal can be precipitated even in a composition range outside of the above described composition ranges but this crystal does not constitute a main crystal phase of a glass-ceramic produced and conductivity of this glass-ceramic is not sufficiently high.

The glasses from which the crystal of $Li_{1+X+Y}M_X Ti_{2-X}Si_YP_{3-Y}O_{12}$ grows have a composition range which is outside of the stoichiometry of the crystal because the content range of $M_2O_3$ in these glasses is 5–10 mol % whereas the stoichiometric content of $M_2O_3$ is less than 5 mol %.

In this system, $SiO_2$ is a very important ingredient. By adding $SiO_2$, the glass forming range is broadened and, moreover, melting property and thermal stability of the glass are improved and an excellent conductivity no less than $10^{-3}$S/cm can be obtained.

A part of Al or Ga may be replaced by one of such trivalent metal elements such as B, In, Sc, Fe and Cr or one of such divalent metal elements as Mg and Zn. Likewise, a part of Ti may be replaced by Zr and a part of Si may be replaced by Ge. In these cases, however, the amount of Al, Ga, Ti or Si replaced by such metal element should not exceed 5%. If the amount of the replaced metal element exceeds 5%, conductivity will drop significantly.

For improving the melting property of the glass, $As_2O_3$, $Sb_2O_3$, $Ta_2O_5$, CdO or PbO may be added. The amount of such ingredient however should not exceed 3%. If the amount of such ingredient exceeds 3%, conductivity of the glass-ceramic will decrease as the amount of addition of the ingredient increases.

A method for manufacturing the conductive glass-ceramics of the $P_2O_5$—$SiO_2$—$TiO_2$—($Al_2O_3$, $Ga_2O_3$)—$Li_2O$ system will now be described.

Starting materials are weighed at a predetermined ratio and mixed uniformly and the mixed materials are thereafter put in a platinum crucible and heated and melted in an electric furnace. First, gas components coming from the raw materials are evaporated at 700° C. and then the temperature is raised to 1400° C. to 1500° C. and the materials are melted at this temperature for about one to two hours. Then, the melt is cast onto a stainless steel plate to form a sheet glass. The glass thus produced is thereafter subjected to heat treatment by heating it under a temperature ranging from 680° C. to 800° C. for about twelve hours and subsequently heating it under a temperature which is higher by 200° C. to 350° C. for about twenty-four hours and glass-ceramics containing $Li_{1+X+Y}M_XTi_{2-X}Si_YP_{3-Y}O_{12}$ as a main crystal phase and having a high lithium ion conductivity is produced.

This two-step heat treatment method is applicable also to the production of the glass-ceramics of the $P_2O_5$—$SiO_2$—$TiO_2$—($Al_2O_3$, $Ga_2O_3$)—$Li_2O$ system. Conversely, the glass-ceramics of the $P_2O_5$—$TiO_2$—($Al_2O_3$, $Ga_2O_3$)—$Li_2O$ system can be produced by employing the one step heat treatment method described above with reference to the glass-ceramics of the $P_2O_5$—$TiO_2$—($Al_2O_3$, $Ga_2O_3$)—$Li_2O$ system.

BRIEF DESCRIPTION OF THE DRAWINGS

In the accompanying drawings.

EXAMPLES

Figure 1:
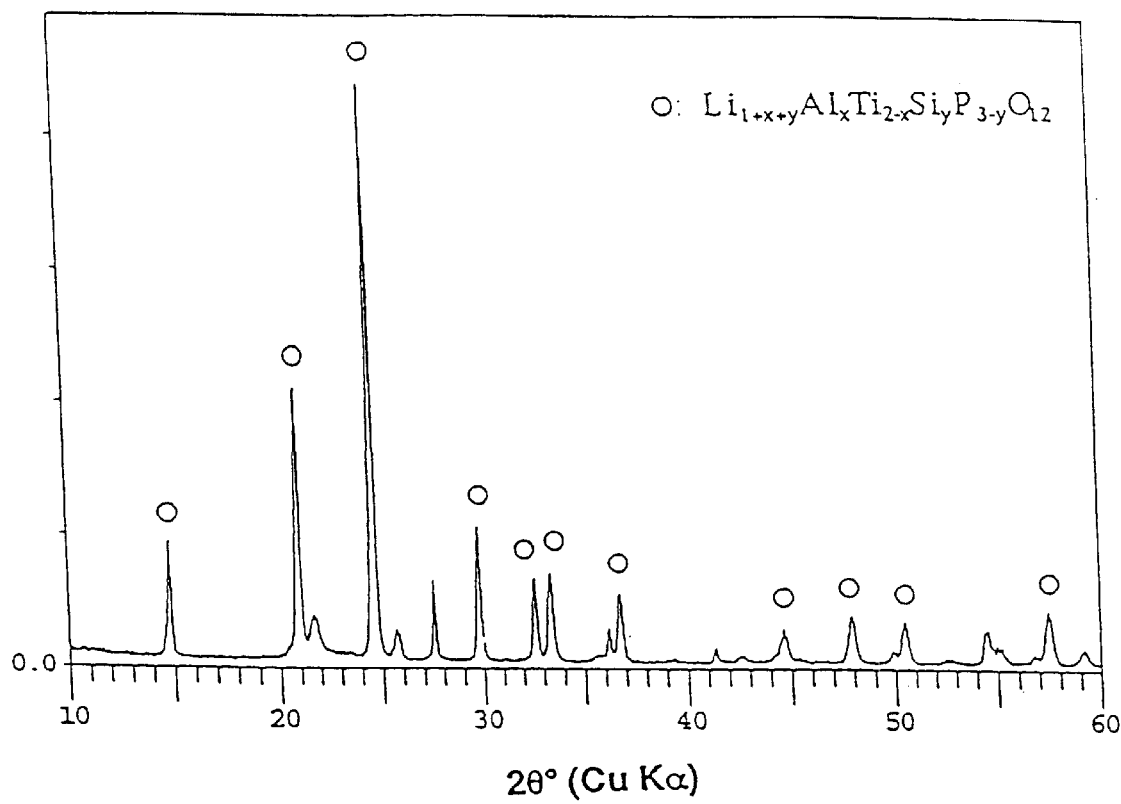
FIG. 1 is a graph showing an X-ray diffraction pattern of Example 3.

Examples of the novel glass-ceramics used as the solid electrolyte of the electric cells and gas sensors of the invention will now be described. It should be noted that these examples are illustrative only and the scope of the invention in no way is restricted by these examples.

Example 1

As starting materials, $NH_4H_2PO_4$, $TiO_2$, $Al(OH)_3$ and $Li_2CO_3$ were used. These starting materials were weighed to constitute a composition of $39P_2O_5$-$8.5Al_2O_3$-$39TiO_2$-$13.5Li_2O$ in mol %. The materials were mixed uniformly and then put in a platinum crucible and heated and melted in an electric furnace. First, $CO_2$, $NH_3$ and $H_2O$ coming from the raw materials were evaporated at 700° C. Then, the temperature was raised to 1450° C. and the materials were melted by heating them at this temperature for 1.5 hour. Thereafter, the melt was cast onto a stainless steel plate to form a uniform sheet glass. The glass was annealed at 550° C. for two hours for removing thermal stress of the glass.

The glass thus produced was cut into specimens each having the size of 20×20 mm. The specimens of glass were polished on both surfaces and subjected to heat treatment under various heat conditions. The crystal phase which precipitated in the specimens was determined by the powder X-ray diffraction method. As a result, it was found that the precipitated crystal phase under all heat conditions was $Li_{1+X}A_XTi_{2-X}(PO_4)_3$. Electrical conductivity of the glass-ceramic was measured within a range from $10^{-2}$–$\times10^{+7}$ Hz by the complex impedance. Resistance of the specimens (sum of grain resistance and grain boundary resistance) was determined from the Cole-Cole Plot and the conductivity was calculated by the equation of $\sigma=(t/A)(1/R)$ (where $\sigma$ is conductivity, t is thickness of the specimen, A is electrode area and R is resistance of the specimen). As a result, the specimen which was heat treated at 1000° C. for 12 hours exhibited the highest conductivity of $1.3\times10^{-3}$S/cm at room temperature (Table 1, Example No. 1).

Example 2

As the starting materials, $NH_4H_2PO_4$,$TiO_2$,$Al(OH)_3$, $Ga_2O_3$ and $Li_2O_3$ were used to produce a glass-ceramic by employing the same manner as in Example 1. The crystal phase which grew in specimens of this glass-ceramic was determined to be $Li_{1+X}(Al,Ga)_XTi_{2-X}(PO_4)_3$. The specimen which was heat treated at 950° C. for 12 hours exhibited the highest conductivity of $1.0\times10^{-3}$S/cm (Table 1,Example No.2).

TABLE 1

| (composition in mol %) | Examples No. | |
|---|---|---|
| | 1 | 2 |
| $P_2O_5$ | 39 | 39 |
| $TiO_2$ | 39 | 38 |
| $Al_2O_3$ | 8.5 | 6.5 |
| $Ga_2O_3$ | | 2.5 |
| $Li_2O$ | 13.5 | 14 |
| conductivity at room temperature(S/cm) | $1.3 \times 10^{-3}$ | $1.0 \times 10^{-3}$ |
| temperature of heat treatment(° C.) | 1000 | 950 |
| time of heat treatment(Hr) | 12 | 12 |

Example 3

As starting materials, $NH_4H_2PO_4$, $SiO_2$, $TiO_2$, $Al(OH)_3$ and $LI_2CO_3$ were used. These starting materials were weighed to constitute a composition of $32P_2O_5$-$8SiO_2$-$41TiO_2$-$5Al_2O_3$-$14Li_2O$ in mol %. The materials were mixed uniformly and then put in a platinum crucible and heated and melted in an electric furnace. First, $CO_2$, $NH_3$ and $H_2O$ coming from the raw materials were evaporated at 700° C. Then the temperature was raised to 1450° C. and the materials were melted by heating them at this temperature for 1.5 hour. Thereafter, the melt was cast onto a stainless steel plate to form a uniform sheet glass. The glass was annealed at 550° C. for two hours for removing thermal stress of the glass.

The glass thus produced was cut into specimens each having the size of 20×20 mm. The specimens of glass were polished on both surfaces and subjected to heat treatment at a temperature of 800° C. for 12 hours and then at 1000° C. for 24 hours to produce a dense glass-ceramic. The crystal phase precipitated in the specimens was determined by the powder X-ray diffraction to be $Li_{1+X;Y}Al_XTi_{2-X}Si_YP_{3-Y}O_{12}$. The glass-ceramic exhibited a very high conductivity of $1.5\times10^{-3}$S/cm at room temperature (Table 2, Example No. 3).

FIG. 1 shows an X-ray diffraction pattern of the glass-ceramic of Example 3.

Examples 4–8

Specimens of glass-ceramics were prepared in a manner similar to Example 3. The compositions and conductivities of these specimens as well as the composition and conductivity of Example 3 are shown in the following Tables 2 and 3.

TABLE 2

(composition in mol %)

| | Examples No. | | |
|---|---|---|---|
| | 3 | 4 | 5 |
| $P_2O_5$ | 32 | 33.5 | 30 |
| $SiO_2$ | 8 | 6 | 10 |
| $TiO_2$ | 41 | 42 | 40 |
| $Al_2O_3$ | 5 | 5 | 5 |
| $Ga_2O_3$ | | | |
| $Li_2O$ | 14 | 13.5 | 15 |
| conductivity at room temperature(S/cm) | $1.5 \times 10^{-3}$ | $1.0 \times 10^{-3}$ | $1.2 \times 10^{-3}$ |

TABLE 3

(composition in mol %)

| | No. | | |
|---|---|---|---|
| | 6 | 7 | 8 |
| $P_2O_5$ | 35 | 32 | 35 |
| $SiO_2$ | 4 | 8 | 4 |
| $TiO_2$ | 38 | 41 | 38 |
| $Al_2O_3$ | 8 | | 5 |
| $Ga_2O_3$ | | 5 | 3 |
| $Li_2O$ | 15 | 14 | 15 |
| conductivity at room temperature(S/cm) | $1.1 \times 10^{-3}$ | $1.2 \times 10^{-3}$ | $1.0 \times 10^{-3}$ |

Example 9

Figure 2:
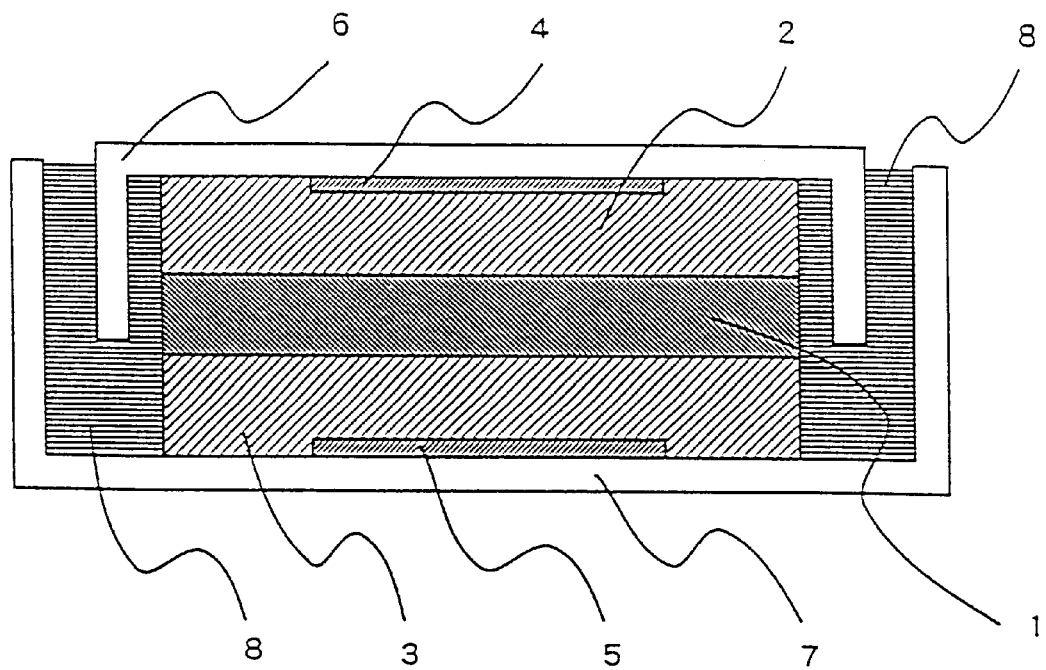
FIG. 2 is a sectional view of an example of a lithium cell using a lithium ion conductive solid electrolyte.

As a typical example of a lithium electric cell, an example of flat type cell is shown in the sectional view of FIG. 2. The cell is composed of a negative electrode container 6, a negative electrode collector 4 constructed of a conductive thin film or a thin film made of aluminum or stainless steel, a negative electrode 2, a lithium ion conductive glass-ceramic layer 1, a positive electrode 3, a positive electrode collector 5 constructed of a conductive thin film or a thin film made of aluminum or stainless steel, a positive electrode container 7 and an insulating filler 8 made of an insulating material such as polypropylene. The negative and positive electrodes 2 and 3 are received in the case formed by the positive and negative electrode containers 6 and 7 in such a manner that these electrodes 2 and 3 oppose each other through the lithium ion conductive glass-ceramic layer 1. The positive electrode 3 is connected to the positive electrode container 7 through the positive electrode collector 5 and the negative electrode 2 is connected to the negative electrode container 6 through the negative electrode collector 4. Chemical energy produced in the cell can be collected as electric energy from terminals of the negative electrode container 6 and the positive electrode container 7.

In constructing the cell made according to the invention, various other materials which are conventionally used for forming a cell can be used except for the solid electrolyte portion.

The lithium ion conductive glass-ceramic layer must be sufficiently thin, i.e., 1 mm or less and preferably 0.5 mm or less. Many reports and proposals have been made about the material of the positive electrode 3 and it is typically made of $LiCoO_2$ or $Li_{1+x}V_3O_8$. Likewise, reports and proposals have been made about the material of the negative electrode 2 and it is typically made of $Li_4Ti_5O_{12}$ or carbon.

As to the positive and negative electrodes 2 and 3 formed on the opposite surfaces of the lithium ion conductive glass-ceramic layer 1 and the collectors 4 and 5 formed in the negative and positive electrodes 2 and 3, these component parts may be preformed respectively and stacked one after another to a composite cell. Alternatively, the positive and negative electrodes 2 and 3 and the collectors 4 and 5 may be formed sequentially by any of suitable known methods including ion sputtering, CVD, screen printing, coating, sol-gel method, ion plating, ion beam evaporation and electron beam evaporation.

As a comparative example, a cell is composed in the same manner as in the above example except that the solid electrolyte is formed by mixing 1.7 mol of titanium oxide, 0.7 mol of lithium carbonate, 3.0 mol of ammonium phosphate and 0.2 mol of aluminum oxide in an agate mortar, press-forming the mixture to pellets and sintering the pellets at 900° C. for two hours, crushing the sintered pellets again in an agate mortar, press-forming the crushed material which has passed a sieve of 400 mesh to pellets again, sintering the pellets at 1000° C. for two hours and processing the sintered pellets to a thin plate.

Example 10

Figure 3:
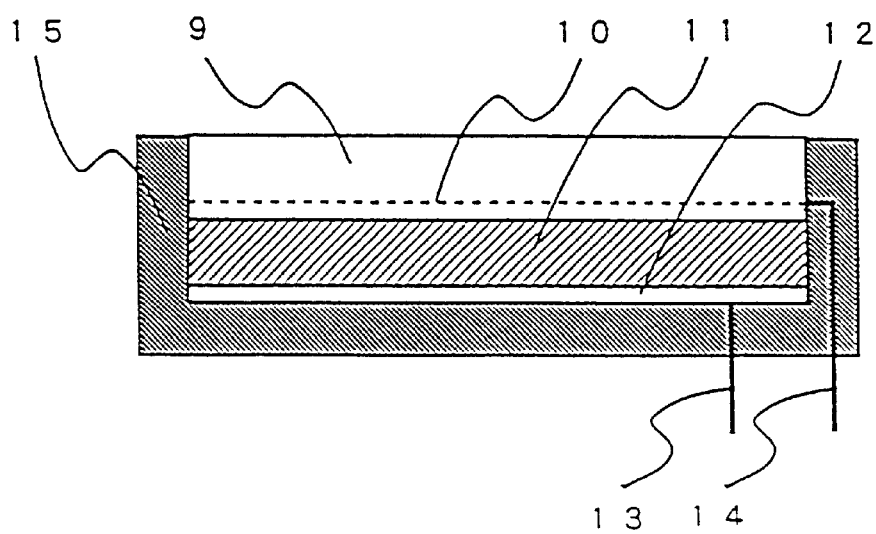
FIG. 3 is a sectional view showing an example of a gas sensor using a lithium ion conductive solid electrolyte.
Figure 4:
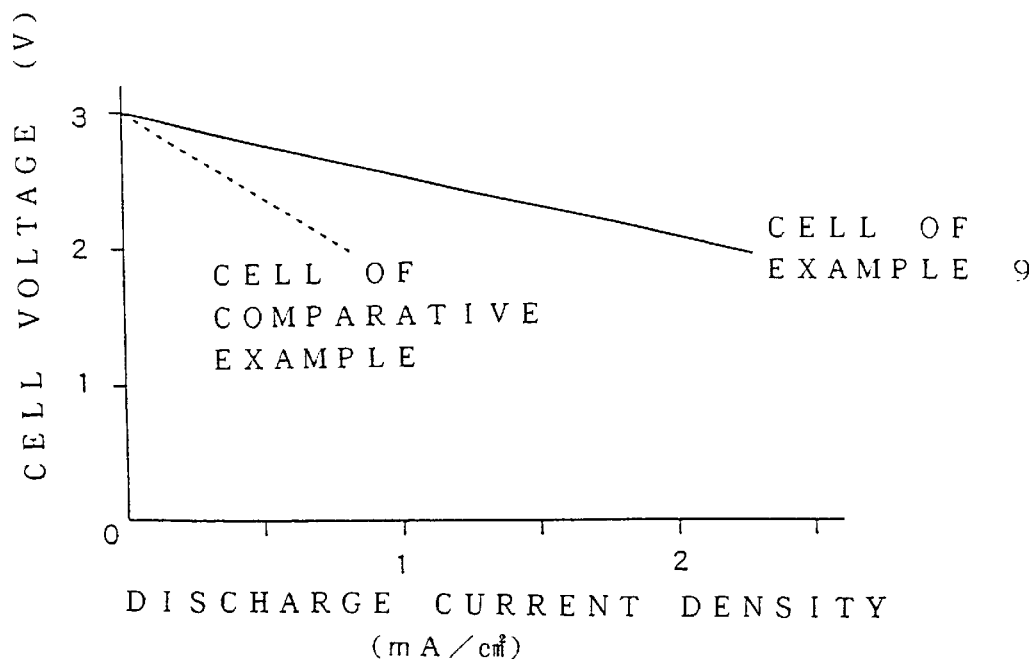
FIG. 4 is a graph showing an effective discharge characteristic of the cell shown in FIG. 2.
Figure 5:
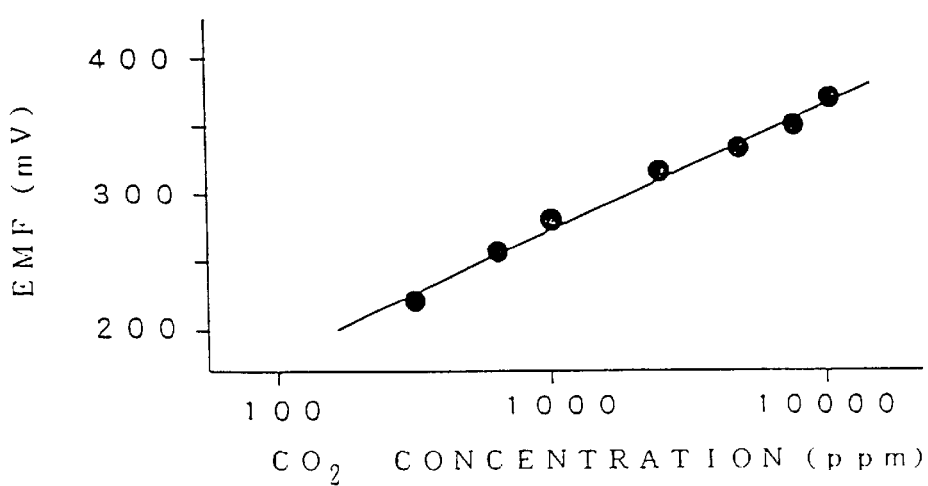
FIG. 5 is a graph showing an electromotive force characteristic by a carbonate gas partial pressure at room temperature of the gas sensor shown in FIG. 3.

As a typical example of a gas sensor, as example of a carbon dioxide gas sensor is shown in section in FIG. 3. The upper and lower surfaces of a lithium ion conductive glass-ceramic layer 11 are polished to provide the layer 11 having a thickness of 1 mm to 2 mm, preferably 1 mm or below and more preferably 0.5 mm or below. On one of the surfaces of the layer 11 (the upper surface in the illustrated example) is formed, by ion sputtering, a layer of metal carbonate, preferably lithium carbonate or mixture of lithium carbonate and other carbonate. A platinum mesh 10 to which a lead 14 is connected is disposed on the surface of this metal carbonate layer to form an electrode. Then, a layer 9 of metal carbonate is formed on the upper surface of the electrode 10 to fix the electrode 10. On the other surface (the lower surface in the illustrated example) of the lithium ion conductive layer 11 is formed, by evaporation, a platinum thin film to form an electrode 12 and a lead 13 is connected to the electrode 12. According to this sensor, an electromotive force corresponding to the concentration of carbon dioxide gas is produced between the two electrodes due to dissociation equilibrium of the carbonate by the carbon dioxide gas in a mixture gas including the carbon dioxide gas and, therefore, the concentration of the carbon dioxide gas can be detected by measuring this electromotive force.

Forming of the carbonate layer and the electrode layers is not limited to the above method but these layers may be formed by other known methods including CVD, screen printing, sol-gel method, ion plating, ion beam evaporation, MBE, vacuum evaporation and electron beam evaporation.

What is claimed is:

1. A solid electric cell comprising a case, a negative electrode, a positive electrode and a solid electrolyte, the negative electrode, positive electrode and solid electrolyte being disposed in the case in such a manner that the negative electrode opposes the positive electrode through the solid electrolyte characterized in that the solid electrolyte is made of a lithium ion conductive glass-ceramic having a crystal phase grow from glasses by heat treating these glasses wherein said glasses have a composition range outside of the stoichiometry of the crystal, and said glass-ceramics being obtained by melting raw materials to a melt, casting the melt to a glass and subjecting the glass to heat treatment.

2. A solid electric cell as defined in claim 1 wherein lithium ion conductive glass-ceramic having ion conductivity no less than $10^{-3}$S/cm at room temperature.

3. A solid electric cell as defined in claim 2 wherein said lithium ion conductive glass-ceramic is poreless.

4. A solid electric cell as defined in claim 1 wherein lithium ion conductive glass-ceramic comprising 38–40 mol % of $P_2O_5$ and containing $Li_{1+x}(Al,Ga)_xTi_{2-x4}(PO_4)_3$ (where 0<X<0.8) as a main crystal phase.

5. A solid electric cell as defined in claim 4 wherein said lithium ion conductive glass-ceramic comprises in mol %:

| | |
|---|---|
| $P_2O_5$ | 38–40% |
| $TiO_2$ | 25–45% |
| $M_2O_3$ (where M is Al or Ga) | 5–15% |
| $Li_2O$ | 10–20%. |

6. A solid electric cell as defined in claim 5 wherein said lithium ion conductive glass-ceramic comprises in mol %:

| | |
|---|---|
| $P_2O_5$ | 38–40% |
| $TiO_2$ | 30–45% |
| $Al_2O_3$ | 5–15% |
| LiO | 10–16%. |

7. A solid electric cell as defined in claim 5 wherein lithium ion conductive glass-ceramic comprises in mol %:

| | |
|---|---|
| $P_2O_5$ | 38–40% |
| $TiO_2$ | 25–45% |
| $Ga_2O_3$ | 5–12% |
| $Li_2O$ | 10–20%. |

8. A solid electric cell as defined in claim 1 wherein said lithium ion conductive glass-ceramic containing $Li_{1+X+Y}M_XTi_{2-X}Si_YP_{3-Y}O_{12}$ where M is Al or Ga 0<X≦0.4 and 0<Y≦0.6), as a main crystal phase.

9. A solid electric cell as defined in claim 8 wherein lithium ion conductive glass-ceramic comprises in mol %:

| | |
|---|---|
| $P_2O_5$ | 26–40% |
| $SiO_2$ | 0.5–12% |
| $TiO_2$ | 30–45% |
| $M_2O_3$ (where M is Al or Ga) | 5–10% |
| $Li_2O$ | 10–18%. |

10. A solid electric cell as defined in claim 9 wherein lithium in conductive glass-ceramic comprises in mol %:

| | |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18%. |

11. A solid electric cell as defined in claim 9 wherein lithium ion conductive glass-ceramic comprises in mol %:

| | |
|---|---|
| $P_2O_5$ | 26–40% |
| $SiO_2$ | 0.5–12% |
| $TiO_2$ | 32–45% |

-continued

| | |
|---|---|
| $Ga_2O_3$ | 5–10% |
| $Li_2O$ | 10–18%. |

12. A gas sensor comprising a case, a negative electrode, a positive electrode, a solid electrolyte and a layer for which an electromotive force corresponding to the concentration of the gas is produced between the two electrodes, a lead connected to the negative electrode and a lead connected to the positive electrode, the negative electrode, positive electrode and solid electrolyte being disposed in the case in such a manner that the negative electrode opposes the positive electrode through the solid electrolyte characterized in that the solid electrode is made of a lithium ion conductive glass-ceramic having a crystal phase grow from glasses by heat treating these glasses wherein said glasses have a composition range outside of the stoichiometry of the crystal, and said glass-ceramics being obtained by melting raw materials to a melt, casting the melt to a glass and subjecting the glass to heat treatment.

13. A gas sensor as defined in claim 12 wherein said lithium ion conductive glass-ceramic having ion conductivity no less than $10^{-3}$S/cm at room temperature.

14. A carbon dioxide gas sensor as defined in claim 13 wherein said layer is a metal carbonate layer.

15. A gas sensor as defined in claim 13 wherein said lithium ion conductive glass-ceramic is poreless.

16. A gas sensor as defined in claim 12 wherein said lithium ion conductive glass-ceramic comprising 38–40 mol % of $P_2O_5$ and containing $Li_{1+x}(Al,Ga)_xTi_{2-x}(PO_4)_3$, where 0<X<0.8, as a main crystal phase.

17. A gas sensor as defined in claim 16 wherein said lithium ion conductive glass-ceramic comprises in mol %:

| | |
|---|---|
| $P_2O_5$ | 38–40% |
| $TiO_2$ | 25–45% |
| $M_2O_3$ (where M is Al or Ga) | 5–15% |
| $Li_2O$ | 10–20%. |

18. A gas sensor as defined in claim 17 wherein said lithium ion conductive glass-ceramic comprises in mol %:

| | |
|---|---|
| $P_2O_5$ | 38–40% |
| $TiO_2$ | 30–45% |
| $Al_2O_3$ | 5–15% |
| $Li_2O$ | 10–16%. |

19. A gas sensor as defined in claim 17 wherein said lithium ion conductive glass-ceramic comprises in mol %:

| | |
|---|---|
| $P_2O_5$ | 38–40% |
| $TiO_2$ | 25–45% |
| $Ga_2O_3$ | 5–12% |
| $Li_2O$ | 10–20%. |

20. A gas sensor as defined in claim 12 wherein said lithium ion conductive glass-ceramic containing $Li_{1+X+Y}M_XTi_{2-X}Si_YP_{3-Y}O_{12}$, where M is Al or Ga 0<X≦0.4 and 0<Y≦0.6 as a main crystal phase.

21. A gas sensor as defined in claim 20 wherein said lithium ion conductive glass-ceramic comprises in mol %:

|  |  |
|---|---|
| $P_2O_5$ | 26–40% |
| $SiO_2$ | 0.5–12% |
| $TiO_2$ | 30–45% |
| $M_2O_3$ (where M is Al or Ga) | 5–10% |
| $Li_2O$ | 10–18%. |

22. A gas sensor as defined in claim 21 wherein said lithium ion conductive glass-ceramic comprises in mol %:

|  |  |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18%. |

23. A gas sensor as defined in claim 21 wherein said lithium ion conductive glass-ceramic comprises in mol %:

|  |  |
|---|---|
| $P_2O_5$ | 26–40% |
| $SiO_2$ | 0.5–12% |
| $TiO_2$ | 32–45% |
| $Ga_2O_3$ | 5–10% |
| $Li_2O$ | 10–18%. |

* * * * *